United States Patent
Jenkins et al.

(10) Patent No.: US 8,753,896 B2
(45) Date of Patent: Jun. 17, 2014

(54) METHOD OF MONITORING A SURFACTANT IN A MICROELECTRONIC PROCESS BY FLUORESCENCE

(75) Inventors: Brian V. Jenkins, Warrenville, IL (US); John E. Hoots, Batavia, IL (US); Amy M. Tseng, Woodridge, IL (US)

(73) Assignee: Nalco Company, Naperville, IL (US)

( * ) Notice: Subject to any disclaimer, the term of this patent is extended or adjusted under 35 U.S.C. 154(b) by 957 days.

(21) Appl. No.: 11/696,760

(22) Filed: Apr. 5, 2007

(65) Prior Publication Data

US 2008/0248577 A1  Oct. 9, 2008

(51) Int. Cl.
*G01N 21/76* (2006.01)
*H01L 21/66* (2006.01)
*G01N 21/00* (2006.01)

(52) U.S. Cl.
CPC ............... *H01L 22/00* (2013.01); *H01L 22/20* (2013.01); *H01L 22/30* (2013.01); *G01N 21/00* (2013.01)
USPC ............... 436/172; 134/1.3; 134/2; 134/25.4; 436/2; 436/101; 436/103; 436/104; 436/163; 436/164; 436/166; 436/55; 438/8

(58) Field of Classification Search
CPC ............. G01N 2021/8411; G01N 2021/8557; G01N 21/272; G01N 35/085; G01N 21/80; G01N 31/221; H01L 22/12
See application file for complete search history.

(56) References Cited

U.S. PATENT DOCUMENTS

| | | | |
|---|---|---|---|
| 5,277,135 A * | 1/1994 | Dubin et al. ................ | 110/345 |
| 6,207,369 B1 * | 3/2001 | Wohlstadter et al. ........ | 435/6.11 |
| 6,238,487 B1 * | 5/2001 | Jenkins et al. ................ | 134/2 |
| 6,337,944 B1 * | 1/2002 | Hofstraat ...................... | 385/143 |
| 2004/0253737 A1 * | 12/2004 | Haberland et al. ............ | 436/55 |

OTHER PUBLICATIONS

Kindy et al., "A sequential injection method for the determination of Tween-80 in natural water samples using a fluorescence enhancement of the dye Eosin-B", Analytical Sciences, vol. 19, pp. 737-742 (May 2003).*

Iwunze et al., "Characterization of Fluorescent Surfactant Aggregates by Fluorimetric and Viscosimetric Techniques", Monatshefte fur Chemie, vol. 128, pp. 585-592 (1997).*

* cited by examiner

*Primary Examiner* — Dirk Bass

(74) *Attorney, Agent, or Firm* — Leydig, Voit & Mayer, Ltd.

(57) ABSTRACT

A method of monitoring a surfactant in a microelectronic process is disclosed. Specifically, the monitoring of a surfactant occurs by studying the fluorescence or electromagnetic emission of a sample collected from a microelectronic process.

28 Claims, No Drawings

METHOD OF MONITORING A SURFACTANT IN A MICROELECTRONIC PROCESS BY FLUORESCENCE

FIELD OF THE INVENTION

The invention pertains to monitoring a surfactant that is added to a process for making a microelectronic component.

BACKGROUND

Surfactants play a pivotal role in the manufacturing of microelectronics. For example, during a photolithography process, surfactants are added to photoresist developers to facilitate their distribution across a wafer's surface. Proper distribution of the photoresist developer is crucial to chip configuration. Therefore, a metrology for surfactants is highly desirable. Presently, current microelectronic processes utilize a sonic surface tension measurement as a metrology for surfactant levels. This metrology suffers drawbacks, which includes low sensitivity to changes in surfactant dosages and being operator dependent. A more sensitive metrology and consistent metrology for surfactant levels are thus desired.

Another example of where surfactants are used in a microelectronic process is in the wet-etching stage of wafer manufacturing. Specifically, surfactants facilitate the dispersal of etchants applied to a wafer during an etching process. By doing so, a microelectronics manufacturer can achieve a more uniform and predictable result during the etching process. Precise control of the concentration of surfactant in the etchant can help achieve a more consistent outcome and therefore a need to monitor surfactants added to a microelectronic process is desired.

SUMMARY OF THE INVENTION

The present invention provides for a method of monitoring a surfactant in a process for making a microelectronic component comprising: adding a surfactant to a process for making a microelectronic component, wherein the surfactant has a fluorescent property; sampling fluid from the process; measuring the fluorescence of the surfactant in the sample; correlating the fluorescence of the surfactant in the sample with the concentration of the surfactant in the process; and optionally taking action to maintain the concentration of the surfactant in the process at a desired level.

The present invention also provides for a method of monitoring a surfactant in a process for making a microelectronic component comprising: adding a surfactant to a process for making a microelectronic component; sampling fluid from the process, wherein sampling includes adding a fluorogenic agent to the sample and forming a reacted surfactant; measuring at least the fluorescence of the reacted surfactant in the sample; correlating the fluorescence of the reacted surfactant with the concentration of the surfactant in the process; and optionally taking action to maintain the concentration of the surfactant in the process at a desired level.

The present invention also provides for a method of monitoring a surfactant in a process for making a microelectronic component comprising: adding a surfactant and a fluorescent tracer to a process for making a microelectronic component, wherein the surfactant has a fluorescent property; sampling fluid from the microelectronic process; measuring the fluorescence of the surfactant and the fluorescent tracer in the sample collected from the microelectronic process; determining the consumption of the surfactant by looking at the difference between the fluorescence of the fluorescent tracer and the fluorescence of the surfactant in the sample; and optionally taking action to maintain the concentration of the surfactant in the process at a desired level.

The present invention also provides for a method of monitoring a surfactant in a process for making a microelectronic component comprising: adding a surfactant and a fluorescent tracer to a microelectronic process; sampling fluid from the microelectronic process; measuring at least the fluorescence of the fluorescent tracer alone or in combination with the surfactant when the surfactant has a fluorescent property; correlating the fluorescence of the fluorescent tracer alone or in combination with the surfactant with the concentration of surfactant added to the process; and optionally taking action to maintain the concentration of surfactant in the process at a desired level.

The present invention also provides for a method of monitoring a surfactant in a process for making a microelectronic component comprising: adding a surfactant to a process for making a microelectronic component, wherein the surfactant is capable of emitting electromagnetic radiation; sampling fluid from the process; measuring the emission of electromagnetic radiation of the surfactant in the sample; correlating the emission of electromagnetic radiation of the surfactant in the sample with the concentration of the surfactant in the process; and optionally taking action to maintain the concentration of the surfactant in the process at a desired level.

The present invention further provides for a method of monitoring a surfactant in a process for making a microelectronic component comprising: adding a surfactant to a process for making a microelectronic component; sampling fluid from the process, wherein sampling includes adding an emission agent to the sample and forming a reacted surfactant; measuring at least the emission of electromagnetic radiation of the reacted surfactant in the sample; correlating the emission of electromagnetic radiation of the reacted surfactant with the concentration of the surfactant in the process; and optionally taking action to maintain the concentration of the surfactant in the process at a desired level.

DETAILED DESCRIPTION OF THE INVENTION

The above-mentioned methodologies may be applied to various stages of a process for making a microelectronic component.

In one embodiment, the process is a photolithography process.

In another embodiment, the process is a wet-etching process.

Sampling fluid from a microelectronic process can occur via various routes.

In one embodiment, fluid is drawn from a process via a side-stream and the sample is subsequently analyzed in a flow cell.

In another embodiment, fluid is sampled subsequent to the addition of surfactant to the process and before application of the surfactant to a wafer.

During the sampling stage the sample can be prepared for measurement as well.

In one embodiment, sampling includes dilution of the sample and/or removal of contaminants from the sample.

In another embodiment, sampling involves a sequential injection analysis ("SIA") of the sample or a segmented flow analysis ("SFA") of the sample.

SFA and SIA techniques are well known to those of ordinary skill in the art and therefore the integration of an SIA or SFA analysis technique can be accomplished without undue experimentation. With respect to sampling, SIA, for example, allows a reagent, e.g. a fluorogenic agent, to be added to sample in an efficient and practical manner. More specifically, SIA provides a method for reducing the amount of a reagent that needs to be added to a sample containing an analyte to provide a given effect that is necessary for analysis of a sample. SIA also involves measurement of the sample.

In another embodiment, sampling involves flow injection analysis ("FIA") of the sample. FIA analysis is known to those of ordinary skill in the art and can be carried out without undue experimentation.

In another embodiment, sampling utilizes a Lab-on-Valve module. In particular, the Lab-on-Valve module is associated with the process for making a microelectronic component. The Lab-on-Valve module serves as a platform upon which a sample can be drawn in, prepared for measurement, e.g. mixing with a reagent, and for implementation of SIA or SFA analysis. An analytical measurement, such as pH of the sample, viscosity of the sample, or conductivity of the sample can be measured with the Lab-on-Valve module. The use of the Lab-on-Valve module in the analytical arts is well known and can be practiced without undue experimentation.

Measuring the fluorescence or emission of electromagnetic radiation of the surfactant in the sample takes place after the sample is collected, which could be right after the sample is collected, after mixing with a reagent, after manipulation of the sample, or after the sample is prepared in any particular manner that allows the fluorescence or emission of electromagnetic radiation of the surfactant to be directly or indirectly measured.

The emission of electromagnetic radiation can be correlated with the concentration of the surfactant. One of ordinary skill in the art would know to how to correlate the emission with the concentration of an analyte. In this case, a surfactant is an analyte of interest.

In another embodiment, the fluorescence of the sample is measured. By measuring the fluorescence of the sample at a specified wavelength(s), the concentration of the surfactant (s) can be determined. The fluorescence of a sample can be measured and the measurement can be correlated with the concentration of the surfactant in the process by one of ordinary skill in the art without undue experimentation.

More specifically, if the surfactant being studied is inherently fluorescent, the fluorescence of the surfactant can be directly measured by one or more fluorometers.

In another embodiment, the surfactant does not fluoresce and therefore a fluorogenic agent needs to be added to the process, or during the sampling stage. The result of adding a fluorogenic agent is the formation of a reacted surfactant (when surfactant is present) that is capable of being measured by fluorescence. An example of a general protocol for making a reacted analyte can be found in U.S. Pat. No. 5,435,969 which is herein incorporated by reference. This case provides an example of making a reacted analyte that is capable of being monitored by fluorescence through the addition of an incorporated reagent which is added to a sample from a process stream.

The type of fluorogenic agent utilized in this protocol depends on the type of surfactant.

In one embodiment, the fluorogenic agent is 4,5,6,7-Tetrachloro-2',4',5',7'-tetraiodofluorescein disodium salt.

Fluorescent tracers may serve as a vehicle for determining the amount of surfactant present in a microelectronic process.

It is known in the art of fluorescent tracer technology to relate the fluorescent signal of a fluorescent tracer to the amount of fluorescent tracer present. Then by knowing the amount of fluorescent tracer present, the amount of chemical present can be calculated, because a known amount of a fluorescent tracer is always added to a known amount of chemical, thus making the proportional relationship between the fluorescent tracer and the chemical added known. When the chemical has fluorescent properties itself the quantity of chemical can be obtained from its fluorescent signal. Also, a combination of monitoring the fluorescence of the chemical itself and fluorescent tracer is another method for determining the quantity of chemical present.

The fluorometer produces an output signal proportional to the detected fluorescence. Optionally, adjusting the dosage of the fluorescent tracer and chemical or chemical alone is based on the output signal from said fluorescent tracer and/or said chemical detected by the fluorometer.

In one embodiment the fluorescent tracer can be inert and is herein referred to as inert fluorescent tracer. The term "inert" as used herein refers to an inert fluorescent tracer that is not appreciably or significantly affected by any other chemistry in the system, or by the other system parameters which include, but are not limited to, pH and temperature. To quantify what is meant by "not appreciably or significantly affected", this statement means that an inert fluorescent compound has no more than a 10% change in its fluorescent signal, under severe conditions in a microelectronic process.

It should be appreciated that a variety of different and suitable inert fluorescent tracers can be utilized in any suitable amount, number and application.

An inert tracer must be transportable with the water of the microelectronic process and thus substantially, if not wholly, water-soluble therein at the concentration it is used, under the temperature and pressure conditions specific and unique to the microelectronic process. In other words, an inert fluorescent tracer displays properties similar to a solute of the microelectronic process in which it is used. In an embodiment, it is preferred that the inert fluorescent tracer of the present invention meet the following criteria:

1. Be substantially foreign to the chemical species that are normally present in the water of the microelectronic process in which the inert fluorescent tracer(s) may be used;
2. Be substantially impervious to interference from, or biasing by, the chemical species that are normally present in the water of the microelectronic process in which the inert tracer(s) may be used;
3. Be compatible with all chemicals added to the water of the microelectronic process in which the inert fluorescent tracer(s) may be used, and thus in no way reduce the efficacy thereof;
4. Be compatible with all components of its formulation; and
5. Be relatively nontoxic and environmentally safe, not only within the environs of the microelectronic process in which it may be used, but also upon discharge therefrom.

It should be appreciated that the amount of inert fluorescent tracer to be added to the microelectronic process that is effective without being grossly excessive can vary with respect to a variety of factors including, without limitation, the monitoring method selected, the extent of background interference associated with the selected monitoring method, the magnitude of the expected inert fluorescent tracer(s) concentration in the microelectronic process, the monitoring mode (such as, an on-line continuous monitoring mode), and other similar factors.

In one embodiment, the amount of tracer added to said microelectronic process ranges from about 5 ppt to about 1000 ppm, preferably from about 1 ppb to about 50 ppm, more preferably from about 5 ppb to about 50 ppb.

In another embodiment, the fluorescent tracer can be added to a microelectronic process as a component of a formulation, rather than as a separate component, such as a dry solid or neat liquid. The fluorescent tracer formulation or product may include an aqueous solution or other substantially homogeneous mixture that disperses with reasonable rapidity in the microelectronic process to which it is added. In this regard, the fluorescent tracer's concentration may be correlated to the concentration of a product.

In another embodiment, the surfactant added to the microelectronic process is tagged with moiety capable of fluorescing.

Monitoring a surfactant can take place on-line.

Monitoring a surfactant can take place at various intervals of time.

In one embodiment, monitoring is continuous, sequential, or at a programmed interval of time.

Various types of surfactants may be utilized during a microelectronic process and therefore, depending on the nature of the surfactant, one or more of the discussed methodologies may be utilized to measure the amount of surfactant in a microelectronic process.

In one embodiment, the surfactant is a cationic surfactant. In a further embodiment, the cationic surfactant is a fluorinated surfactant.

In another embodiment, the surfactant is non-ionic surfactant. In a further embodiment, the non-ionic surfactant is a fluorinated surfactant.

Other types of surfactants may be studied as well, such as an anionic surfactant, an amphoteric surfactant, and a zwitterionic surfactant.

The surfactants may be monitored alone or in combination with one another.

When measuring the fluorescence of a surfactant directly or indirectly, one or more process variables may be measured in conjunction with the fluorescence measurement.

In one embodiment the process variable(s) are selected from the group consisting of: pH of said process stream; conductivity of said process stream; viscosity of said process stream; and a combination thereof.

Various types of fluorogenic agents can be utilized in this protocol.

In one embodiment, the fluorogenic agent is 4,5,6,7-Tetrachloro-2',4',5',7'-tetraiodofluorescein disodium salt.

One or more agents can be added to the sample to adjust the fluorescent signal positively or negatively. For example, either signal from the fluorescence of the surfactant itself and/or the reacted surfactant can be adjusted either positively or negatively.

In one embodiment, at least one modifying agent positively affects the signal and is a cationic agent selected from the group consisting of: tertiary amines; quaternary amines; tetramethylammonium hydroxide; tetrabutylammonium chloride; cetyltrimethylammonium bromide; and a combination thereof.

In another embodiment, the modifying agent positively affects the signal and is an anionic agent that contains at least one of the following functional groups: sulfonate, carboxylate, or phosphonate.

In another embodiment, if a fluorescent signal is weak then an enhancer can be added to the sample to positively augment the fluorescent signal associated with the surfactant and/or the reacted surfactant.

An inverse protocol may be applied as well. Specifically a modifying agent that quenches a fluorescent signal is added, and then the decrease in fluorescence of the surfactant and/or reacted surfactant is correlated with the concentration of the surfactant.

The methodology for enhancing/quenching a fluorescent signal can occur via different routes.

In one embodiment, a modifying agent is coupled with a fluorogenic agent and then the resulting product is added to a sample potentially containing surfactant and then the fluorescence of the sample is measured at a specified wavelength(s).

In another embodiment, a complex containing an enhancer component and a fluorogenic component are added to sample potentially containing surfactant and the fluorescence of the sample is measured at a specified wavelength(s).

Various types of surfactants, fluorogenic agents, and modifying agents may be used in combination with one another.

In one embodiment, the fluorogenic agent is 4,5,6,7-Tetrachloro-2',4',5',7'-tetraiodofluorescein disodium salt is added to sample containing non-ionic surfactant. In a further embodiment, a modifying agent can be added to this combination to enhance or quench the signal.

In another embodiment, a modifying agent is coupled with fluorogenic agent and then is coupled with a surfactant.

In another embodiment, the fluorogenic agent is 4,5,6,7-Tetrachloro-2',4',5',7'-tetraiodofluorescein disodium salt is added to sample containing non-ionic surfactant.

In response to surfactant levels, action can be taken to maintain the concentration of surfactant in the microelectronic process at a desired level. This can be done via a wide variety of mechanisms. For example, a controller could process information from the one or more analytical devices and respond by implementing a predetermined protocol. Moreover, the controller may be in communication with a pumping mechanism that controls the flow of surfactant into the process stream. The use of controller makes on-line monitoring of the process stream.

In another embodiment, after the sample is measured it is then discharged to a drain or a collection container.

The following examples are not meant to be limiting and are prophetic examples.

EXAMPLES

With respect to dilution ratio (X:Y), the first number refers to the total volume and the second number refers to primary species of interest being diluted. Therefore, if you dilute Y with X, then the first number would be the total volume of X, the volume of species of interest would be Y, and the volume of diluent species (or carrier fluid) would be X−Y. MAX refers to maximum and MN refers to minimum.

Example I

Company A uses Surfactant B in photolithography process for manufacturing of microelectronic circuits. Surfactant B solution is diluted 200.1 (volume/volume) with Carrier Fluid C and the two solutions are mixed to obtain typical use dosage of Surfactant B. A sample of Solution D (solution of 0.5% volume/volume Surfactant B and 99.5% volume/volume Carrier Fluid C) is then withdrawn as a side-stream from the mixing and dilution equipment. Solution D is then sampled by SIA equipment and then the sample is drawn into the holding coil of the SIA equipment, the sample is diluted, and a reagent is added/mixed into the sample. The sample is then sent through a flowcell where it is fluorometrically monitored, and the fluorescent signal of Surfactant B solution is then measured (or alternatively dilution ratio of surfactant is determined . . . e.g., 0.5% volume/volume=200:1 dilution ratio or 1.0% volume/volume=100:1 dilution ratio). The SIA equipment sends an electrical signal that is proportional to Surfactant B solution dosage to the dilution dosing and mixing equipment in order to determine whether to add more or less of Surfactant B solution (based on the control method and control limits). The sample is then discharged to drain and a new sample is drawn into the SIA equipment to begin a new analysis cycle. In this example, the Surfactant B solution setpoint is 200:1 dilution (0.5% volume/volume) with an upper control limit of 205:1 dilution (0.0488% volume/volume) and lower control limit of 195:1 dilution (0.513% volume/volume). A series of analysis readings and responses of dilution control system are listed below.

TABLE 1

Surfactant B Solution Dosage (with SIA analysis and dosage control)

| Analysis # | Surfactant B Dilution (volume/volume) | Surfactant B Solution Dosage (volume/volume) | Control Signal Response |
|---|---|---|---|
| 1 | 200:1 | 0.500% | No change |
| 2 | 204:1 | 0.490% | No change |
| 3 | 203:1 | 0.493% | No change |
| 4 | 206:1 | 0.485% | Surfactant B addition rate increased |
| 5 | 201:1 | 0.498% | No change |
| 6 | 196:1 | 0.510% | No change |
| 7 | 194:1 | 0.515% | Surfactant B addition rate decreased |
| 8 | 197:1 | 0.508% | No change |
| 9 | 200:1 | 0.500% | No change |
| 10 | 198:1 | 0.505% | No change |
| 11 | 193:1 | 0.518% | Surfactant addition rate decreased |
| 12 | 197:1 | 0.508% | No change |
| 13 | 198:1 | 0.505% | No change |
| 14 | 199:1 | 0.503% | No change |
| Average | 199:1 | 0.503% | |
| Max | 206:1 | 0.518% | |
| Min | 193:1 | 0.485% | |
| +/−Sigma | +/−3.7:1 | +/−0.009% | |

Table 1 shows much better control of Surfactant B solution dosage (dilution average is very close to setpoint: 200:1 (0.500%) vs. 199:1 (0.503%). Max and Min values [193:1 (0.518%) and 206:1 (0.485%)] are also very close to control band range of 195:1 (0.513%) to 205:1 (0.488%). Table 2 (monitoring only, without dosage control) shows much higher variability, increased deviation from setpoint and higher Max/lower Min dosage values (as compared to Table 1).

TABLE 2

Surfactant B Solution Dosage (with SIA analysis and no dosage control)

| Analysis # | Surfactant B Dilution (volume/volume) | Surfactant B Solution Dosage (volume/volume) | Control Signal Response |
|---|---|---|---|
| 1 | 200:1 | 0.500% | None |
| 2 | 196:1 | 0.510% | None |
| 3 | 192:1 | 0.521% | None |
| 4 | 185:1 | 0.541% | None |
| 5 | 180:1 | 0.556% | None |
| 6 | 182:1 | 0.549% | None |
| 7 | 195:1 | 0.513% | None |
| 8 | 192:1 | 0.521% | None |
| 9 | 187:1 | 0.535% | None |

TABLE 2-continued

Surfactant B Solution Dosage (with SIA analysis and no dosage control)

| Analysis # | Surfactant B Dilution (volume/volume) | Surfactant B Solution Dosage (volume/volume) | Control Signal Response |
|---|---|---|---|
| 10 | 195:1 | 0.513% | None |
| 11 | 200:1 | 0.500% | None |
| 12 | 202:1 | 0.495% | None |
| 13 | 201:1 | 0.498% | None |
| 14 | 206:1 | 0.485% | None |
| Average | 194:1 | 0.517% | |
| Max | 206:1 | 0.556% | |
| Min | 180:1 | 0.485% | |
| +/−Sigma | +/−7.9:1 | +/−0.021% | |

Example II

Surfactant Dosage Control Based on Inert Fluorescent Tracer

Company A uses Surfactant B in photolithography process for manufacturing of microelectronic circuits. Surfactant B solution also contains 20 ppm of an inert fluorescent tracer. Surfactant B solution which also includes an inert fluorescent tracer is diluted 200:1 (volume/volume) with Carrier Fluid C and the two solutions are mixed to obtain a typical use dosage of Surfactant B. A sample of Solution D (solution of 0.5% volume/volume Surfactant B which also includes a corresponding 1 ppm of inert fluorescent tracer and 99.5% volume/volume Carrier Fluid C) is withdrawn as a side-stream from the mixing and dilution equipment. Solution D is sampled by SIA equipment. A sample is drawn into the holding coil of the SIA equipment, the sample is diluted, and a reagent is added/mixed into the sample. The sample is then sent through a flowcell where the sample is fluorometrically monitored, and the fluorescent of Surfactant B solution is measured (or alternatively dilution ratio of surfactant is determined . . . e.g., 0.5% volume/volume=200:1 dilution ratio or 1.0% volume/volume=100:1 dilution ratio). The SIA equipment sends an electrical signal that is proportional to Surfactant B solution dosage to the dilution dosing and mixing equipment in order to determine whether to add more or less of Surfactant B solution (based on the control method and control limits). The SIA equipment also measures inert fluorescent tracer dosage via fluorescence of the inert fluorescent tracer, and correlates the inert fluorescent tracer dosage to level Surfactant B dilution by Carrier Fluid C to produce Solution D. The sample is then discharged to drain and a new sample is drawn into SIA equipment to begin a new analysis cycle. In this example, the Surfactant B solution setpoint is 200:1 dilution (0.5% volume/volume) with an upper control limit of 205:1 dilution (0.0488% volume/volume) and lower control limit of 195:1 dilution (0.513% volume/volume). A series of analysis readings and responses of dilution control system are listed below:

TABLE 3

Surfactant B Solution Dosage (with SIA analysis and dosage control based on inert fluorescent tracer)

| Analysis # | Surfactant B Solution Dilution* (volume/volume) | Surfactant B Solution Dosage* (volume/volume) | Inert Fluorescent Tracer (ppm) | Solution B Dilution** (volume/volume) | Solution B Dosage** (volume/volume) | Control Signal Response (based on inert tracer in Solution B) |
|---|---|---|---|---|---|---|
| 1 | 200:1 | 0.500% | 0.100 | 200:1 | 0.500% | No change |
| 2 | 204:1 | 0.490% | 0.098 | 204:1 | 0.490% | No change |
| 3 | 203:1 | 0.493% | 0.099 | 202:1 | 0.495% | No change |
| 4 | 206:1 | 0.485% | 0.097 | 206:1 | 0.485% | Surfactant B addition rate increased |
| 5 | 201:1 | 0.498% | 0.100 | 200:1 | 0.500% | No change |
| 6 | 196:1 | 0.510% | 0.102 | 196:1 | 0.510% | No change |
| 7 | 194:1 | 0.515% | 0.103 | 194:1 | 0.515% | Surfactant B addition rate decreased |
| 8 | 197:1 | 0.508% | 0.102 | 196:1 | 0.510% | No change |
| 9 | 200:1 | 0.500% | 0.100 | 200:1 | 0.500% | No change |
| 10 | 198:1 | 0.505% | 0.101 | 198:1 | 0.505% | No change |
| 11 | 193:1 | 0.518% | 0.104 | 192:1 | 0.520% | Surfactant addition rate decreased |
| 12 | 197:1 | 0.508% | 0.102 | 196:1 | 0.510% | No change |
| 13 | 198:1 | 0.505% | 0.101 | 198:1 | 0.505% | No change |
| 14 | 199:1 | 0.503% | 0.101 | 198:1 | 0.505% | No change |
| Average | 199:1 | 0.503% | 0.101 ppm | 199:1 | 0.504% | |
| Max | 206:1 | 0.518% | 0.104 ppm | 206:1 | 0.520% | |
| Min | 193:1 | 0.485% | 0.097 ppm | 192:1 | 0.485% | |
| +/−Sigma | +/−3.7:1 | +/−0.009% | 0.002 ppm | +/−3.8:1 | +/−0.009% | |

*Based on surfactant dosage
**Based on inert fluorescent tracer dosage

Table 3 shows much better control of Surfactant B solution dosage (dilution average is very close to setpoint: 200:1 (0.500%) vs. 199:1 (0.504%). Max and Min values [192:1 (0.520%) and 206:1 (0.485%)] are also very close to control band range of 195:1 (0.513%) to 205:1 (0.488%). In Table 3, surfactant dosage, inert tracer dosage, or a combination of surfactant dosage and inert tracer dosage could be used to monitor and/or control dilution (or dosage) of Surfactant B solution. Table 4 (monitoring only, without dosage control) shows much higher variability, increased deviation from setpoint, and higher Max/lower MIN dosage values (as compared to Table 1).

TABLE 4

Surfactant B Solution Dosage (with SIA analysis and no dosage control)

| Analysis # | Surfactant B Dilution (volume/volume) | Surfactant B Solution Dosage (volume/volume) | Control Signal Response |
|---|---|---|---|
| 1 | 200:1 | 0.500% | None |
| 2 | 196:1 | 0.510% | None |
| 3 | 192:1 | 0.521% | None |
| 4 | 185:1 | 0.541% | None |
| 5 | 180:1 | 0.556% | None |
| 6 | 182:1 | 0.549% | None |
| 7 | 195:1 | 0.513% | None |
| 8 | 192:1 | 0.521% | None |
| 9 | 187:1 | 0.535% | None |
| 10 | 195:1 | 0.513% | None |
| 11 | 200:1 | 0.500% | None |
| 12 | 202:1 | 0.495% | None |
| 13 | 201:1 | 0.498% | None |
| 14 | 206:1 | 0.485% | None |
| Average | 194:1 | 0.517% | |
| Max | 206:1 | 0.556% | |
| Min | 180:1 | 0.485% | |
| +/−Sigma | +/−7.9:1 | +/−0.021% | |

Example III

Finding Error in Surfactant Solution Preparation Based on Analysis of Surfactant and Inert Fluorescent Tracer Dosages Company A uses Surfactant B in photolithography process for manufacturing of microelectronic circuits. Surfactant B solution also contains 20 ppm of an inert fluorescent tracer. Surfactant B solution which also includes an inert fluorescent tracer is diluted 200:1 (volume/volume) with Carrier Fluid C and the two solutions are mixed to obtain typical use dosage of Surfactant B. However, an error occurred during addition of surfactant to prepare Surfactant B solution and only ½ of the ideal dosage of Surfactant B was present. The inert fluorescent tracer was added at the expected dosage to Surfactant B solution. Due to the error in surfactant solution preparation, the ratio of inert tracer to surfactant dosage was 2× higher than expected. When traced Surfactant B (which also includes a corresponding 20 ppm of inert fluorescent tracer solution) was diluted 200:1 with a Carrier Solution C, the corresponding diluted Solution D was prepared.

The Solution D was withdrawn as a side-stream from the mixing and dilution equipment. Solution D was sampled by SIA equipment. A sample was drawn into the holding coil of the SIA equipment, the sample was diluted and a reagent is added/mixed (as needed) into the sample. The sample is then sent through a flowcell where the sample is fluorometrically monitored, and based on the fluorescence of Surfactant B and the inert tracer solutions the dosages of Surfactant B and inert tracer were measured (or alternatively dilution ratios of surfactant and inert tracer were determined). The SIA equipment measures the Surfactant B dosage (or dilution ratio) and compared it to the corresponding inert fluorescent tracer dosage (or dilution ratio) to determine if both dosages (or dilution ratios) were within a prescribed setpoint and control range. The SIA equipment readings for Solution D indicated that the inert fluorescent tracer was at the correct dosage (and at the corresponding correct dilution level), whereas the surfactant dosage was ½ of the expected (and at 2× the expected dilution level) . . . due to the error in the preparation of the original Surfactant B Solution (listed above).

Since the SIA equipment readings indicated the inert fluorescent tracer was at the correct dosage, then this indicates that dilution equipment mixing Solution B with Carrier Solution C was working correctly. Therefore, because the surfactant dosage was ½ of the expected dosage and the dilution equipment was working correctly based on the inert fluorescent tracer readings and the SIA equipment is working properly then there was an error in preparation of the original Surfactant solution B. More specifically, the use of the SIA equipment to measure surfactant and inert fluorescent tracer dosages allowed the problem to be clearly and quickly identified as an error in preparation of the original Surfactant solution B (½ of the proper amount of surfactant was added). Corrective measures can be quickly implemented and the erroneous Solution B was quickly replaced in order to prevent any damage to process equipment and prevent any reduction in performance of the corresponding product being manufactured.

The invention claimed is:

1. A method of controlling concentration of a diluted surfactant fluid within a desired dilution ratio prior to application of the diluted surfactant fluid to a microelectronic component during manufacture of the microelectronic component comprising:
creating a diluted surfactant fluid by combining a surfactant and a carrier fluid prior to application of the diluted surfactant fluid to the microelectronic component, wherein the surfactant is capable of fluorescence;
sampling the diluted surfactant fluid prior to application of the diluted surfactant fluid to the microelectronic component;
creating a conditioned sample b further diluting the sampled diluted surfactant fluid;
measuring the fluorescence of the surfactant in the conditioned sample;
correlating the measured fluorescence of the surfactant in the conditioned sample with the concentration of the surfactant in the sampled diluted surfactant fluid; and
if the correlation in the previous step indicates that the sampled diluted surfactant fluid is not within the desired dilution ratio, taking action to adjust the concentration of the surfactant in the diluted surfactant fluid so the fluid is within the desired dilution ratio prior to application of the diluted surfactant fluid to the microelectronic component; and
if the correlation in the previous step indicates that the sampled diluted surfactant fluid is within the desired dilution ratio, applying the diluted surfactant fluid onto the microelectronic component.

2. The method of claim 1, wherein the process is a photolithography process.

3. The method of claim 1, wherein the process is a wet-etching process.

4. The method of claim 1, wherein the process is controlled on-line.

5. The method of claim 1, wherein the sampling involves an SIA analysis of the sample or an SFA analysis of the sample.

6. The method of claim 1, wherein the sampling utilizes a LOV module for a sample analysis.

7. The method of claim 1, wherein the sampling further comprises removal of contaminants from the sampled diluted surfactant fluid.

8. The method of claim 1 wherein the surfactant is a cationic surfactant.

9. The method of claim 8 wherein the surfactant is a fluorinated surfactant.

10. The method of claim 1, wherein the surfactant is a non-ionic surfactant.

11. The method of claim 10 wherein the surfactant is a fluorinated surfactant.

12. The method on claim 1, wherein the controlling is continuous, sequential, or at a programmed interval.

13. The method of claim 1, wherein sampling includes measuring an additional process variable, optionally wherein the process variable includes at least one of the following process variables: pH of the process; conductivity of the process stream; and viscosity of the process stream.

14. A method of controlling concentration of a diluted surfactant fluid within a desired dilution ratio prior to application of the diluted surfactant fluid to a microelectronic component during manufacture of the microelectronic component comprising:
creating a diluted surfactant fluid by combining a surfactant and a carrier fluid prior to application of the diluted surfactant fluid to the microelectronic component;
sampling the diluted surfactant fluid prior to application of the diluted surfactant fluid to the microelectronic component;
creating a conditioned sample by further diluting the sampled diluted surfactant fluid and adding a fluorogenic agent capable of reacting with the surfactant;
measuring at least the fluorescence of the reacted surfactant in the conditioned sample;
correlating the measured fluorescence of the reacted surfactant in the conditioned sample with the concentration of the surfactant in the sampled diluted surfactant fluid; and
if the correlation in the previous step indicates that the sampled diluted surfactant fluid is not within the desired dilution ratio, taking action to adjust the concentration of the surfactant at a desired dilution ratio in the diluted surfactant fluid so the fluid is within the desired dilution ratio prior to application of the diluted surfactant fluid; and
if the correlation in the previous step indicates that the sampled diluted surfactant fluid is within the desired dilution ratio, applying the diluted surfactant fluid onto the microelectronic component.

15. The method of claim 14, wherein the fluorogenic agent is 4,5,6,7-Tetrachloro-2',4',5',7'-tetraiodofluorescein disodium salt.

16. The method of claim 14, further comprising adding at least one modifying agent to the sampled diluted surfactant fluid and/or the conditioned sample, which modifies the fluorescence of the reacted surfactant positively.

17. The method of claim 16, wherein said modifying agent is a cationic agent selected from the group consisting of: a tertiary amine; a quaternary amine; tetramethylammonium hydroxide; tetrabutylammonium chloride; cetyltrimethylammonium bromide; and combinations thereof.

18. The method of claim 16, wherein the modifying agent is an anionic agent comprising at least one of the following functional groups: a sulfonate, a carboxylate, and a phosphonate.

19. The method of claim 14 wherein said surfactant is a cationic surfactant.

20. The method of claim 15 wherein said surfactant is a cationic surfactant.

21. The method of claim 14, wherein said surfactant is a non-ionic surfactant.

22. The method of claim 16, wherein said surfactant is a non-ionic surfactant.

23. A method of controlling concentration of a diluted surfactant fluid within a desired consumption factor prior to application of the diluted surfactant fluid to a microelectronic component during manufacture of the microelectronic component comprising:
creating a diluted surfactant fluid by combining a surfactant, a fluorescent tracer, and a carrier fluid prior to application of the diluted surfactant fluid to the microelectronic component, wherein the surfactant is capable of fluorescence;
sampling the diluted surfactant fluid prior to application of the diluted surfactant fluid to the microelectronic component;
creatine a conditioned sample b further diluting the sampled diluted surfactant fluid;
measuring the fluorescence of the surfactant and the fluorescence of the fluorescent tracer in the conditioned sample;
determining a consumption factor of the surfactant by comparing the fluorescence of the fluorescent tracer and the fluorescence of the surfactant in the conditioned sample; and
if the consumption factor in the previous step indicates that the sampled diluted surfactant fluid is being consumed at an undesired rate, taking action to adjust the concentration of the surfactant in the diluted surfactant fluid so the fluid is within the desired consumption factor prior to application of the diluted surfactant fluid to the microelectronic component; and
if the consumption factor in the previous step indicates that the sampled diluted surfactant fluid is within the desired consumption factor, applying the diluted surfactant fluid onto the microelectronic component.

24. The method of claim 23, wherein the fluorescent tracer is an inert fluorescent tracer.

25. A method of controlling concentration of a diluted surfactant fluid within a desired dilution ratio prior to application of the diluted surfactant fluid to a microelectronic component during manufacture of the microelectronic component comprising:
creating a diluted surfactant fluid by combining a surfactant a fluorescent tracer and a carrier fluid prior to application of the diluted surfactant fluid to the microelectronic component;
sampling the diluted surfactant fluid prior to application of the diluted surfactant fluid to the microelectronic component;
creating a conditioned sample b further diluting the sampled diluted surfactant fluid;
measuring in the conditioned sample at least the fluorescence of the fluorescent tracer alone or in combination with the surfactant if the surfactant is capable of fluorescence;
correlating the measured fluorescence of the fluorescent tracer alone or in combination with the surfactant with the concentration of the surfactant in the sampled diluted surfactant fluid; and
if the correlation in the previous step indicates that the sampled diluted surfactant fluid is not within the desired dilution ratio taking action to adjust the concentration of the surfactant in the diluted surfactant fluid so the fluid is within the desired dilution ratio prior to application of the diluted surfactant fluid to the microelectronic component and
if the correlation in the previous step indicates that the sampled diluted surfactant fluid is within the desired dilution ratio, applying the diluted surfactant fluid onto the microelectronic component.

26. The method of claim 25, wherein said fluorescent tracer is an inert fluorescent tracer.

27. A method of controlling concentration of a diluted surfactant fluid within a desired dilution ratio prior to application of the diluted surfactant fluid to a microelectronic component during manufacture of the microelectronic component comprising:
creating a diluted surfactant fluid by combining a surfactant and a carrier fluid prior to the application of the diluted surfactant fluid to the microelectronic component, wherein the surfactant is capable of emitting electromagnetic radiation;
sampling the diluted surfactant fluid prior to application of the diluted surfactant fluid to the microelectronic component;
creatine a conditioned sample b further diluting the sampled diluted surfactant fluid;
measuring the emission of electromagnetic radiation of the surfactant in the conditioned sample;
correlating the measured emission of electromagnetic radiation of the surfactant in the conditioned sample with the concentration of the surfactant in the sampled diluted surfactant fluid; and
if the correlation in the previous step indicates that the sampled diluted surfactant fluid is not within the desired dilution ratio, taking action to adjust the concentration of the surfactant in the diluted surfactant fluid so the fluid is within the desired dilution ratio prior to application of the diluted surfactant fluid to the microelectronic component; and
if the correlation in the previous step indicates that the sampled diluted surfactant fluid is within the desired dilution ratio, applying the diluted surfactant fluid onto the microelectronic component.

28. A method of controlling concentration of a diluted surfactant fluid within a desired dilution ratio prior to application of the diluted surfactant fluid to a microelectronic component during manufacture of the microelectronic component comprising:
creating a diluted surfactant fluid by combining a surfactant and a carrier fluid prior to application of the diluted surfactant fluid to the microelectronic component;
sampling the diluted surfactant fluid prior to application of the diluted surfactant fluid to the microelectronic component;
creating a conditioned sample by further diluting the sampled diluted surfactant fluid and adding an emission a eg capable of reacting with the surfactant and emitting electromagnetic radiation as a result of the reaction;
measuring at least the emission of electromagnetic radiation of the reacted surfactant in the conditioned sample;
correlating the measured emission of electromagnetic radiation of the reacted surfactant with the concentration of the surfactant in the sampled diluted surfactant fluid; and
if the correlation in the previous step indicates that the sampled diluted surfactant fluid is not within the desired dilution ratio, taking action to adjust the concentration of the surfactant in the diluted surfactant fluid so the fluid is within the desired dilution ratio prior to application of the diluted surfactant fluid to the microelectronic component; and if the correlation in the previous step indicates that the sampled diluted surfactant fluid is within the desired dilution ratio, applying the diluted surfactant fluid onto the microelectronic component.

* * * * *

UNITED STATES PATENT AND TRADEMARK OFFICE
CERTIFICATE OF CORRECTION

PATENT NO.       : 8,753,896 B2
APPLICATION NO.  : 11/696760
DATED            : June 17, 2014
INVENTOR(S)      : Brian V. Jenkins et al.

Page 1 of 1

It is certified that error appears in the above-identified patent and that said Letters Patent is hereby corrected as shown below:

In the Claims

Column 11 in claim 1, line 37, "sample b further" should be --sample by further--

Column 13 in claim 23, line 19, "creatine a conditioned sample b" should be --creating a conditioned sample by--

Column 13 in claim 25, line 48, a --,-- should be inserted after "surfactant"

Column 13 in claim 25, line 66, a --,-- should be inserted after "ratio"

Column 14 in claim 25, line 3, a --;-- should be inserted after "component"

Column 14 in claim 27, line 23, "creatine a conditioned sample b" should be --creating a conditioned sample by--

Column 14 in claim 28, line 55, "emission a eg capable" should be --emission agent capable--

Signed and Sealed this
Ninth Day of September, 2014

Michelle K. Lee
*Deputy Director of the United States Patent and Trademark Office*